United States Patent
Bose

(10) Patent No.: US 7,816,141 B2
(45) Date of Patent: Oct. 19, 2010

(54) MODIFIED FREEZE FRACTURE DIRECT IMAGING APPARATUS AND TECHNIQUE

(75) Inventor: Arijit Bose, Lexington, MA (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 1087 days.

(21) Appl. No.: 11/338,566

(22) Filed: Jan. 24, 2006

(65) Prior Publication Data

US 2006/0177935 A1    Aug. 10, 2006

Related U.S. Application Data

(60) Provisional application No. 60/646,474, filed on Jan. 24, 2005.

(51) Int. Cl.
    *G01N 33/00* (2006.01)
(52) U.S. Cl. .......................................................... 436/5
(58) Field of Classification Search ...................... 436/5
    See application file for complete search history.

(56) References Cited

U.S. PATENT DOCUMENTS

2002/0001855 A1*    1/2002    Prentiss et al. ............... 436/526

OTHER PUBLICATIONS

Semmler et al., High-pressure freezing causes structural alterations in phospholipid model membranes, 1998, Journal of Microscopy, v. 190, p. 317-327.*
Lepault et al., Electron microscopy of frozen biological suspensions, 1983, Journal of Microscopy, v. 129, p. 89-102.*

* cited by examiner

*Primary Examiner*—Lore Jarrett
(74) *Attorney, Agent, or Firm*—Gauthier & Connors LLP

(57) ABSTRACT

A modified freeze direct imaging of a viscous surfactant mesophase method. A chamber is provided having controlled temperature and solvent partial pressure. The chamber has two copper planchettes at the top and bottom thereof. A sample is placed in the chamber on a grid and is squeezed between the planchettes into a thin film. The thin film is placed in a liquid to vitrify the sample. The sample is removed from the planchettes to fracture the sample. The sample is then placed on a cold stage; and imaged.

12 Claims, 1 Drawing Sheet

Schematic of proposed environment controlled unit for sample preparation using FFDI.

Illustration of the FFDI technique.

Schematic of proposed environment controlled unit for sample preparation using FFDI.

MODIFIED FREEZE FRACTURE DIRECT IMAGING APPARATUS AND TECHNIQUE

PRIORITY INFORMATION

The present application is a continuation application of Provisional Patent Application No. 60/646,474 filed with the United States Patent and Trademark Office on Jan. 24, 2005.

This invention was made with government support under NSF Grant No. 9909912 date Jan. 1999-Apr. 2004.

BACKGROUND OF THE INVENTION

1. Field of the Invention

This invention is directed to a modified freeze fracture imaging of a viscous surfactant mesophase.

2. Description of the Prior Art

Surfactants have an ability to self assemble into a wide variety of supramolecular structures such as micelles, bilayers, vesicles, liquid crystals, and emulsions. Self-assembly has become an important avenue for employing and fabricating nanostructures with useful electrical, optical, chemical and mechanical properties. Some factors that determine the specific type of aggregate formed by a surfactant in a solvent include the alkyl chain length, nature of solvent, surfactant concentration, temperature, salt concentration, and the presence of one or more cosurfactants. A wide range of aggregate structures and morphologies can be obtained in a mixed surfactant system. For example, aqueous mixtures of cationic and anionic surfactants form a variety of composition dependent microstructures including spherical micelles, worm-like micelles, vesicles and lamellar phases. The templating effect offered by the surfactant aggregates has been a proven tool for material synthesis. Mesoporous zeolites, porous polymers, biomimetic ceramics, and a range of other inorganic structures with different architecture can be synthesized within these templated systems. The various classes for templating have been classified as synergistic, transcriptive and reconstructive.

The ability to 'visualize' microstructures and examine morphologies is vital if these aggregates are to be used for guiding synthesis. One approach is to image in reciprocal space, using neutron, X-ray or light scattering, from which orientationally averaged morphologies can be obtained. While these techniques are very useful and look at a statistically large amount of sample, they rely on inversion from reciprocal space to real space to uncover morphologies, and are therefore model-dependent and sometimes not unique. The ability to generate direct images would serve as an extremely powerful complement to any scattering data. However, direct imaging of aggregates in solutions poses significant challenges. The length scales being probed fall into the range suitable for electron microscopy. Clearly, the sample cannot be exposed to the vacuum in an electron microscope, since all the solvent will evaporate. Surfactant aggregates are not electron dense, so staining with heavy metal salts is sometimes used. However, the addition of salts can have a dramatic impact on phase behavior. Therefore special techniques are required for artifact-free visualization using electron microscopy. These include cryogenic methods such as freeze frame transmission electron microscopy known as freeze fracture TEM (FFTEM) and cryogenic transmission electron microscopy (cryo-TEM). FFTEM is predicated upon rapid freezing of the sample, passing a fracture plane through aggregates, successful replication of the fracture surface and liftoff of the replica for direct visualization. This is a laborious technique, and is critically dependent on fracture planes passing through representative sections of the sample. What is observed is the surface topology along the fracture plane. In cryo-TEM, the sample is placed on a specially prepared microscope grid, thinned by blotting, and then vitrified by direct contact with the cryogen. If the sample has a large organic content, contact with the ethane cryogen causes dissolution, and restricts the ability to use normal cryo-TEM techniques for non destructive imaging. Additionally, highly viscous systems such as gels, cannot be thinned down by blotting. Freeze fracture direct imaging (FFDI) combines features of FETEM and cryo-TEM, arid alleviates many of these problems.

Freeze fracture direct imaging (FFDI) has been used to image microstructures present in a highly viscous four-component mesophase containing water, isooctane, AOT [bis(2-ethylexyl) sodium sulfosuccinate], and lecithin. As water is added to a fixed amount of a ternary solution of isooctane and the two surfactants, the microstructure evolves from a water-in-oil microemulsion, to a highly viscous columnar hexagonal, and then to multilamellar vesicles. Each of these microstructures is imaged directly. Previous small-angle neutron scattering measurements have identified the lamellar phase, but the FFDI technique demonstrates that these are onionlike curved multilamellar. structures rather than planar bilayers. Freeze fracture direct imaging expands the range of cryo-transmission microscopy to highly viscous, high-organic-content systems that typically have been difficult to visualize. One reference describing the FFDI method is Freeze Fracture Direct Imaging of a Viscous Surfactant Mesophase, Agarwal, et 2003

SUMMARY OF THE INVENTION

A modified freeze fracture direct imaging method wherein an environmental chamber having a controlled temperature and solvent partial pressure is used control the environment in which the sample is being tested. A caliper/forceps is used to bring the copper planchettes together but at a controlled speed to minimize shearing. A liquid nitrogen cooled knife is used to fracture the sample between the copper planchettes and the grid.

One object of the invention is to provide an environmental chamber having a controllable temperature such that a sampler can be evaluated at a temperature other than ambient.

Another object of the invention is to provide a caliper used to control the speed in which the samples are compressed to minimize any shearing.

Still another object of the invention is the use of a nitrogen cooled knife to fracture the sample between the copper planchettes and the grid.

BRIEF DESCRIPTION OF THE DRAWINGS

These and other features of the present invention will now be described in greater detail with reference to the accompanying drawings, wherein.

DETAILED DESCRIPTION OF THE INVENTION

Figure 2:
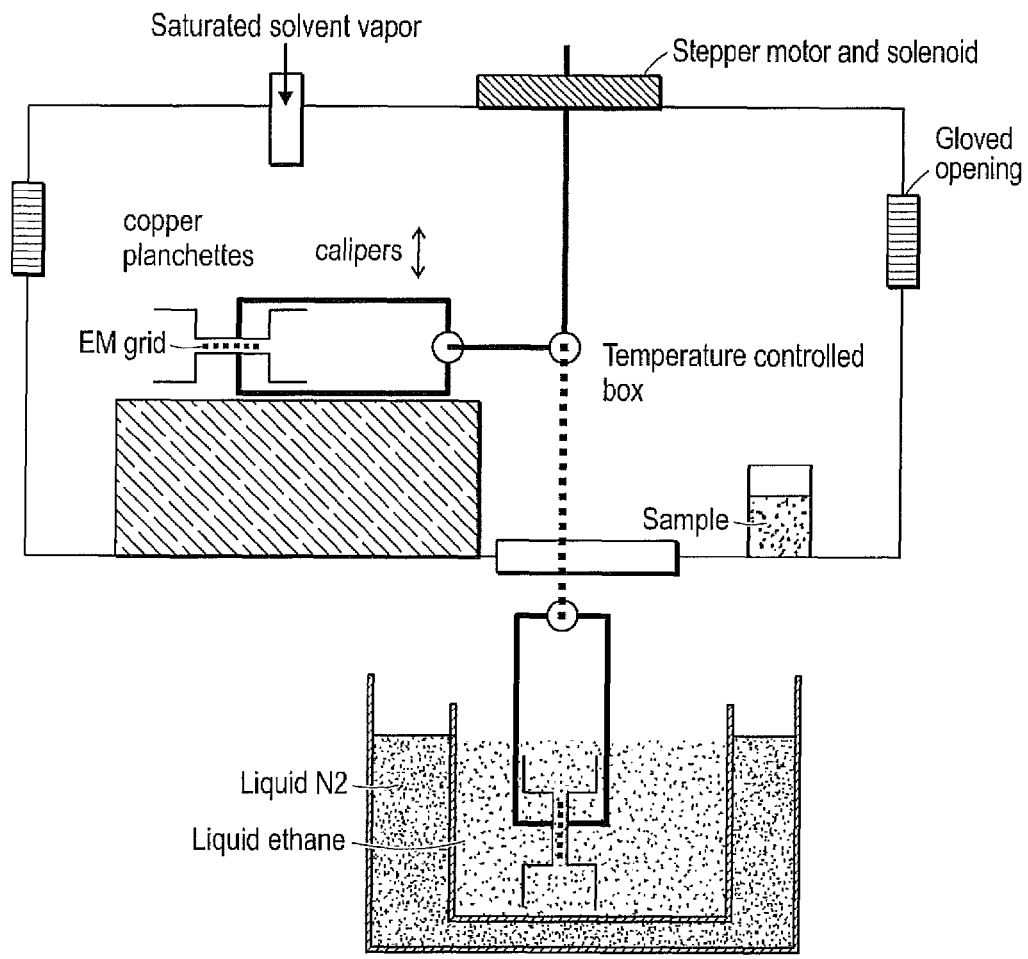
FIG. 2 a schematic of the proposed apparatus.

The current FFDI method has deficiencies. It is inconvenient to handle and does not permit samples to be evaluated at temperatures other than ambient. The method described herein, called Modified Freeze Fracture Direct Imaging (MFFDI) resolves these issues. The key features are (i) an environmental chamber with controlled temperature and solvent partial pressure, along with easy access to the sample, (ii) a specially designed caliper/forcep that allows the copper planchettes to be brought together firmly but at a controlled slow speed to minimize any shearing of high viscosity samples, (iii) a liquid nitrogen cooled knife that is used to fracture the sample between the copper planchettes and the grid. A schematic of the proposed apparatus is shown in FIG. 2. Once the sample is thinned by closing the caliper, the hinged rod holder lifts the assembly upwards, locks the assembly in a vertical position and plunges it through a shutter into liquid ethane. Opening of the caliper fractures one surface. The grid is released from the other planchette using a cold knife, lifted using a liquid nitrogen cooled tweezer and stored under liquid nitrogen until subsequent viewing on a cold stage.

By applying a potential on one of the copper planchettes relative to a ground on the microscope grid, we will observe how electric fields affect microstructures (either directly or by electroosmotic flow in the nanochannels) in these systems. The system can be vitrified with the electric field applied, so relaxation effects can be eliminated. Similarly, magnetic field gradients can be applied on a sample containing paramagnetic particles. Magnetophoretic migration will affect the orientation of the nanoscale microstructures in this system, allowing a highly anisotropic material to be made. The images will therefore be true representations of field-induced microstructures.

Figure 1:
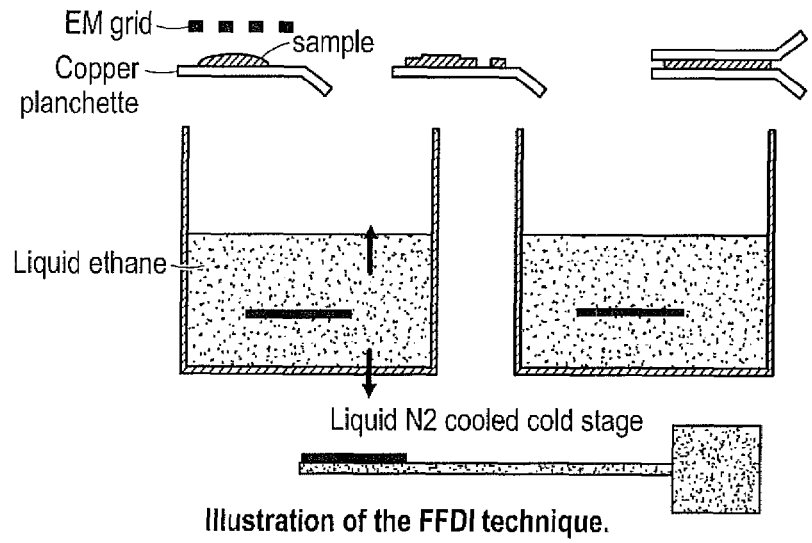
FIG. 1 is an illustration of the modified FFDI technique including the sample.

The sample is placed on a grid, two copper planchettes at the top and bottom squeeze the sample into a thin film. If the sample viscosity is low, it imbibes into the grid by capillary action when the sandwich assembly is lowered into the solution. The sandwiched assembly is dropped into liquid ethane, vitrifying the sample. The planchettes are separated from the grid, fracturing the sample (FIG. 1). The sample is placed on a cold stage (at −170 C, prevents sublimation, amorphous to crystalline transitions and beam damage) and imaged directly at a slight underfocus to enhance phase contrast.

This imaging method does not use any heavy metal salts to create contrast, therefore avoiding salt-related phase transitions. It can delineate differences between various regions within an object, rather than just contrast differences between the object and background, thus providing much better resolution than conventional TEM. However, current FFDI setup does not permit sample preparation at conditions other than room temperature. This greatly limits the range of samples that can be imaged using this technique. This invention describes a system that permits the artifact-free imaging of viscous and high organic content samples over an extensive temperature range. Since microstructures are very critically temperature-dependent, this will be a very useful device and method.

The specialty chemical, material science industries may use this technique to determine microstructures of templates used for creating new materials organized from nano to microscopic scales. For example, the knowledge of surfactant aggregate microstructures is critical toward predicting the performance of commercial detergents, paint rheology modifiers, polymer-based drug delivery systems, and templates for materials synthesis. By using this method, soft aggregates in viscous liquids or in organic solvents can be directly images without distortion from the native states.

Although the present invention has been shown and described with respect to several preferred embodiments thereof, various changes, omissions and additions to the form and detail thereof, may be made therein, without departing from the spirit and scope of the invention.

What is claimed is:

1. A modified freeze fracture direct imaging of a viscous surfactant mesophase method, said method comprising:
   providing an environmental chamber having controlled temperature and solvent partial pressure, said chamber having two copper planchettes at the top and bottom;
   placing a viscous sample in the chamber on a grid;
   without blotting the sample, squeezing the sample between the planchettes into a thin film;
   placing the thin film into a liquid to vitrify the sample;
   removing the sample from the planchettes to fracture the sample;
   placing the sample on a cold stage; and
   imaging the sample.

2. The method of claim 1, wherein the liquid is ethane.

3. The method of claim 1, wherein a liquid nitrogen cooled knife is used to fracture the sample from between the copper plates.

4. The method of claim 1, wherein the sample is examined at varied temperatures.

5. The method of claim 1, wherein the speed and pressure of the squeezing of the sample is controlled.

6. The method of claim 1, wherein the planchettes are copper.

7. The method of claim 1, wherein a saturated solvent is placed within the environmental chamber.

8. The method of claim 1, wherein the cold stage is nitrogen cooled.

9. The method of claim 1, wherein the sample is vitrified by applying a potential on one of the planchettes relative to ground on the grid.

10. The method of claim 1, wherein a magnetic field gradient is applied to a sample having paramagnetic particles.

11. The method of claim 1, wherein the sample placed into the chamber is highly viscous.

12. The method of claim 1, wherein the sample contains surfactants.

* * * * *